United States Patent [19]
Rosenberg et al.

[11] Patent Number: 5,990,100
[45] Date of Patent: Nov. 23, 1999

[54] COMPOSITION AND METHOD FOR TREATMENT OF PSORIASIS

[75] Inventors: E. William Rosenberg, Memphis, Tenn.; Thomas M. Glenn, Mobile, Ala.; Robert B. Skinner, Jr., Memphis; Patricia W. Noah, Germantown, both of Tenn.

[73] Assignees: Panda Pharmaceuticals, L.L.C., Memphis; The University of Tennessee Research Corporation, Knoxville, both of Tenn.

[21] Appl. No.: 09/143,146

[22] Filed: Aug. 28, 1998

Related U.S. Application Data

[63] Continuation-in-part of application No. 09/046,851, Mar. 24, 1998, Pat. No. 5,886,038.

[51] Int. Cl.$^6$ .................................................. A61K 31/595
[52] U.S. Cl. ...................... 514/174; 514/552; 514/863; 514/168
[58] Field of Search .................. 514/168, 174, 514/552, 863

[56] References Cited

U.S. PATENT DOCUMENTS

| | | | |
|---|---|---|---|
| 4,316,902 | 2/1982 | Yu et al. | 424/266 |
| 4,495,203 | 1/1985 | Grollier et al. . | |
| 4,496,588 | 1/1985 | Bey et al. . | |
| 4,507,321 | 3/1985 | Raisfeld . | |
| 4,513,011 | 4/1985 | Grollier et al. . | |
| 4,518,789 | 5/1985 | Yu et al. . | |
| 4,626,529 | 12/1986 | Grollier . | |
| 4,837,213 | 6/1989 | Caron et al. . | |
| 4,847,257 | 7/1989 | Hupe et al. . | |
| 4,892,888 | 1/1990 | Grollier et al. . | |
| 4,933,330 | 6/1990 | Jorgensen et al. . | |
| 4,981,681 | 1/1991 | Tosti . | |
| 5,681,835 | 10/1997 | Willson . | |

FOREIGN PATENT DOCUMENTS 0 513 832  11/1992  European Pat. Off. .

OTHER PUBLICATIONS

"Psoriasis Patients Try the Alternatives", *Skin & Allergy News*, vol. 28, No. 3, dated prior to Mar. 18, 1997, pp. 1 & 25.

*1997 CIR Compendium*, Cosmetic Ingredient Review, Washington, D.C., 1997, p. 97.

Program Bulletin for *Joint Meeting, 5th European Congress on Psoriasis, 7th International Psoriasis Symposium*, received Aug. 17, 1998, p. 24 Paragraph Pl.

Federal Register, vol. 47, No. 233, Part IV, Department of Health and Human Services, FDA, OTC Drug Products for the Control of Dandruff, Seborrheic Dermatitis, and Psoriasis; Establishment of a Monograph, Dec. 3, 1982, pp. 54646–54684.

"A Super–Effective Natural Therapy for Psoriasis", *Health & Healing*, vol. 7, No. 2, By Dr. Julian Whitaker, Feb. 1997, pp. 4–5.

*The Schoch Letter*, vol. 47, No. 4, Editor: Ervin Epstein, Apr. 1997, Paragraphs 49, 50.

Kragballe Pharmacol. Toxicol. (Copenhagen), 77 (4), 241–6 (Abstract), 1995.

*Primary Examiner*—James H. Reamer
*Attorney, Agent, or Firm*—Pearne, Gordon, McCoy & Granger LLP

[57] ABSTRACT

Pharmaceutical compositions and methods for use in the treatment of psoriasis, having isopropyl myristate as a first active ingredient and a different anti-psoriatic agent as a second active ingredient; preferably they are combined in the same pharmaceutical composition.

36 Claims, No Drawings

COMPOSITION AND METHOD FOR TREATMENT OF PSORIASIS

This application is a continuation-in-part of U.S. application Ser. No. 09/046,851, filed on Mar. 24, 1998 now U.S. Pat. No. 5,886,038, the contents of which are incorporated herein by reference in their entirety.

FIELD OF THE INVENTION

This invention relates to pharmaceutical compositions and more particularly to pharmaceutical compositions and methods for use in the treatment of psoriasis.

DESCRIPTION OF RELATED ART

Psoriasis is a chronic skin disease or condition characterized by circumscribed red patches covered with white scales. Conventional treatment compositions include corticosteroid, calcipotriol, and retinoid creams. Coal tar, salicylic acid, zinc pyrithione, and anthralin compositions are also known. U.S. Pat. Nos. 4,513,011; 4,495,203; 4,507,321; 4,933,330; 4,847,257; 4,496,588; 4,981,681; and 4,518,789, the contents of which are incorporated herein by reference, disclose compositions for the treatment of psoriasis. See also U.S. FDA OTC Drug Monograph, Federal Register, Vol. 47, No. 233 (Dec. 3, 1982) pp. 54646–54684, the contents of which are incorporated by reference, which lists OTC compositions for treatment of psoriasis.

Isopropyl myristate has been known as an excipient or vehicle for cosmetic creams and topical medicinals for many years, particularly where good absorption through the skin is desired. However, isopropyl myristate has not been known as an active ingredient or agent for the treatment of psoriasis. There is a need for a more effective composition and method for the treatment of psoriasis.

SUMMARY OF THE INVENTION

A pharmaceutical composition for use in the treatment of psoriasis comprising (a) 0.0001 to 30 weight percent of an anti-psoriatic agent selected from the group consisting of hydrocortisone, other corticosteroids, calcipotriol, retinoids, tar, sulfur, imidazoles, salicylic acid, 4-aminosalicylic acid, 5-aminosalicylic acid, zinc pyrithione, anthralin and its derivatives, ammoniated mercury, allantoin, menthol, phenol, undecylenate compounds, spermidine, spermine, putrescine, 5-amino or substituted amino 1,2,3-triazoles, halomethyl derivatives of a-amino acids, phenyl alpha-acyloxyacetamides, resorcin, eosin, and mixtures thereof and (b) 15 to 97 weight percent isopropyl myristate, said component (a) being present in an effective anti-psoriatic weight percent. The pharmaceutical composition is in a form suitable for topical administration to a human and is selected from the group consisting of a cream, an ointment, a lotion, a liniment, a gel, a solution, a suspension, a paste, a stick, a spray, an aerosol, a shampoo, a soap, a hair conditioner, and a powder. A method of treating psoriasis comprising topically administering to a human having psoriasis (a) an effective amount of an anti-psoriatic agent and (b) an effective amount of isopropyl myristate, the amount of said anti-psoriatic agent in combination with the amount of said isopropyl myristate being effective to treat said psoriasis, said anti-psoriatic agent being present in a topically acceptable pharmaceutical composition, said isopropyl myristate being present in a topically acceptable pharmaceutical composition.

DETAILED DESCRIPTION OF THE PREFERRED EMBODIMENTS OF THE INVENTION

As used herein, parts are parts by weight and percents are weight percents unless otherwise indicated or apparent. When a preferred range such as 5–25 is given, this means preferably at least 5 and preferably not more than 25. An anti-psoriatic agent is an agent for treating psoriasis.

The (a) isopropyl myristate and (b) anti-psoriatic agents are supplied, preferably together, in a pharmaceutically acceptable vehicle for topical administration. Such topically acceptable pharmaceutical compositions include a cream, an ointment, a lotion, a liniment, a gel, a solution, a suspension, a paste, a stick, a spray, an aerosol, a shampoo, a soap, a hair conditioner, and a powder. The composition of these vehicles is known in the art.

The isopropyl myristate is preferably present in the invented pharmaceutical compositions in a weight percent of at least, or equal to, 15, 20, 25, 30, 35, 38, 40, 45, 50, 55, or 60 weight percent and preferably not more than 55, 60, 65, 70, 75, 80, 85, 90, 95 or 97 weight percent. The isopropyl myristate is preferably present in a weight percent of 15–97, more preferably 15–90, more preferably 25–60, more preferably 38–60, more preferably 38–55, more preferably 38–50, more preferably 38–45, alternatively 40, weight percent.

The preferred anti-psoriatic agents and their preferred weight percents in the invented pharmaceutical compositions are as follows (Table 1) (These weight percents are effective anti-psoriatic weight percents).

|  | PREFERRED WEIGHT PERCENT | LESS PREFERRED WEIGHT PERCENT | LESS PREFERRED WEIGHT PERCENT |
| --- | --- | --- | --- |
| 1. Hydrocortisone | 0.05–1 | 0.005–2.5 | 0.001–5 |
| 2. Other corticosteroids | 0.05–1 | 0.005–2.5 | 0.001–5 |
| 3. Calcipotriol | 0.005 | 0.001–0.01 | 0.0001–0.1 |
| 4. Retinoids | 0.05–0.1 | 0.02–0.2 | 0.001–0.5 |
| 5. Tar | 1–7 | 0.5–10 | 0.1–30 |
| 6. Sulfur | 5–10 | 3–14 | 1–20 |
| 7. Imidazoles | 1–2 | 0.5–5 | 0.1–10 |
| 8. Salicylic acid and 4- or 5-aminosalicylic acid | 4–5 | 2–10 | 0.5–20 |
| 9. Zinc pyrithione | 1–2 | 0.5–5 | 0.1–10 |
| 10. Anthralin and its derivatives | 0.25–1 | 0.1–2 | 0.01–4 |
| 11. Ammoniated mercury | 5 | 2–10 | 0.25–20 |

The tar is preferably coal tar, juniper tar, birch tar, pine tar, vegetable tar or mineral tar. The more preferable agents in Table 1 are corticosteroids, calcipotriol and retinoids, more preferably corticosteroids and calcipotriol. The term corticosteroids includes the various corticosteroids currently known for treating psoriasis. Hydrocortisone is a corticosteroid. It is contemplated that as new anti-psoriatic agents are discovered they should be added to Table 1.

The less preferred anti-psoriatic agents, which are known in the art, are allantoin, menthol, phenol, undecylenate compounds, spermidine, spermine, putrescine, 5-amino or substituted amino 1,2,3-triazoles, halomethyl derivatives of a-amino acids, phenyl alpha-acyloxyacetamides, resorcin and eosin, preferably present in the invented composition in weight percents of 0.05–10, more preferably 0.5–5, more preferably 1–2 weight percent, which are effective anti-psoriatic weight percents. The above known anti-psoriatic agents may also be included in known topically acceptable pharmaceutical compositions at known weight percents.

It has been discovered that isopropyl myristate is an active agent for treating psoriasis and it has been discovered that when isopropyl myristate (first active agent) is combined with a known anti-psoriatic agent (second active agent) as taught herein, the resulting multi-active-agent composition is more effective in treating psoriasis than either agent by itself. Preferably the isopropyl myristate active agent and the known anti-psoriatic agent are combined in the same topically acceptable pharmaceutical composition, which composition is topically administered to a human having psoriasis. Less preferably, the isopropyl myristate is in one topically acceptable pharmaceutical composition and the known anti-psoriatic agent is in a separate and different topically acceptable pharmaceutical composition, but both compositions are topically administered to the patient.

The (a) isopropyl myristate (in the preferred weight percents indicated) and (b) known anti-psoriatic agent (in the preferred weight percents indicated) are preferably combined and supplied in a single pharmaceutically acceptable vehicle for topical administration. Less preferably they are supplied in separate vehicles as discussed but are both administered to the patient. The preferred vehicle has the following preferred formulation.

| INGREDIENT | PREFERRED PARTS BY WEIGHT | LESS PREFERRED PARTS BY WEIGHT | LESS PREFERRED PARTS BY WEIGHT |
|---|---|---|---|
| 1. Sodium lauryl sulphate | 0.1 | 0.05–0.2 | 0–2 |
| 2. Polysorbate 80 | 1.5 | 0.8–2 | 0–5 |
| 3. Water | 3.4 | 1.5–10 | 0.8-60 |
| 4. Ethanol | 55 | 35–60 | 5-75 |

Sodium lauryl sulphate and Polysorbate 80 (polyoxyethylene (20) sorbitan monooleate) are emulsifiers (also sometimes referred to as dispersants or surfactants) to help solubilize or emulsify or disperse the isopropyl myristate and/or anti-psoriatic agent in the vehicle. Isopropyl myristate is very soluble or miscible in ethanol and when the vehicle is predominantly ethanol or other alcohol, the emulsifiers may be unnecessary and omitted. As water forms a greater percent of the vehicle, emulsifiers may be necessary to emulsify or solubilize the isopropyl myristate and/or anti-psoriatic agent. Suitable emulsifiers are known in the art, including the various Tween compounds, the various ethanolamines such as triethanolamine, the various SPAN compounds, dioctyl sodium sulfosuccinate, Celouacrogols, Tensides, etc. These emulsifiers may be used singlely or in combination. The emulsifiers preferably form less than 3 or 5 or 10 weight percent of the formulation.

The water/ethanol vehicle is preferably a combination of water and alcohol, such as 25/75, 50/50, or 75/25 water to alcohol (w/w) The vehicle may optionally be all water (emulsifiers as needed) or all alcohol, or any combination inbetween. For example, the vehicle may be at least or at most or equal to 10, 20, 30, 40, 50, 60, 70, 80, or 90 weight percent water, with the balance alcohol, and emulsifiers as needed. The more water, the greasier the formulation. The more alcohol, the greater the formulation will dry out the skin. Both extremes should be avoided. Emollients, humectants, and other customary additives may be added. Sufficient water should be added (such as at least 3, 5 or 8 weight percent) to prevent the alcohol from unduly drying the skin, and to reduce the flammability of the vehicle. The flash point will be increased, making the product less hazardous to make and use.

Ethanol, preferably 96% ethanol, is the preferred alcohol. Less preferably isopropyl alcohol may be used or other common alcohols, or combinations thereof. Preferably at least 25, 30, 35, 40, 45, 50, 55, or 60 weight percent of the composition is formed from water, ethanol, isopropyl alcohol, or any combination thereof, preferably the combination of water and ethanol.

A preferred pharmaceutical composition according to the invention is, by weight percent, 40% isopropyl myristate, 0.005% calcipotriol, 0.1% sodium lauryl sulphate, 1.5% Polysorbate 80, 3.4% water, and about 55% ethanol. Other preferred compositions are prepared by combining isopropyl myristate (in the preferred weight percents indicated) and one of the anti-psoriatic agents listed (in the preferred weight percents indicated) in a vehicle such as the preferred water/ethanol vehicle identified above.

Less preferably the (a) isopropyl myristate active agent or active ingredient and (b) anti-psoriatic active agent or active ingredient, preferably in the concentrations or weight percents noted above or in weight percents appropriate considering the weight percents above and weight percents customary in the other vehicles, may be provided to the patient in other pharmaceutically acceptable vehicles for topical administration known in the art. For example, the vehicle may be an oil system, such as fat or oil or synthetic fat such as petrolatum. The vehicle may be (1) a lotion, such as water and fat or oil with an emulsifier and with or without a little ethanol (with customarily a lower concentration of the active ingredients); (2) a cream or cream base, which is generally the same as a lotion but with less water and a higher viscosity and customarily a higher concentration of the active ingredients; (3) an ointment, which is generally the same as a cream but without the water; it is nearly 100% oil or fat; (4) a gel, which is normally water only with maybe a little ethanol but without fat or oil; a thickening agent is added to provide the gel viscosity; (5) a foam, which is generally an emulsified type of cream; or (6) a solution or suspension of water or ethanol or a combination, such as described in the preferred formulations set forth above, without fat or oil, and with an emulsifier as needed. The pharmaceutical compositions including the (a) isopropyl myristate and/or (b) anti-psoriatic agent are supplied in a form suitable for topical administration, such as those described above, alternatively a liniment, a paste, a stick, an aerosol, a shampoo, a soap, a hair conditioner, or a powder.

The components of the composition or formulation are blended and combined as known in the art. Additional customary inert or inactive additives known in the art may be added. See, for example, U.S. Pat. No. 4,933,330. The compositions are applied as similar compositions are applied, preferably by spraying from a pump sprayer or rubbing into the area affected by psoriasis one, two or three times per day.

The following Examples 1–3, which were conceived and completed prior to Jul. 1, 1998, further illustrate various aspects of the invention.

EXAMPLE 1

A 52 year old man had been using 0.005 weight percent calcipotriol ointment with limited success on lesions of psoriasis for some months. Two comparable plaques of psoriasis were identified in relatively symmetrical areas of his left and right legs. The patient was instructed to continue twice daily applications of the calcipotriol ointment to the spots on both legs but to add a twice daily aerosolized application of a product containing, by weight, 40% isopropyl myristate, 0.1% sodium laurel sulphate, 1.5% Polysorbate 80, 3.4% water, and 55% ethanol to one leg only.

The patient returned two weeks later and said that the addition of the isopropyl myristate product had improved the one leg treated with it plus calcipotriol ointment, while the leg treated with calcipotriol ointment alone was not much changed. The patient was examined without knowing which leg was treated with both products and which with only one. The left leg was clearly better than the right. Pictures were taken. The patient then said that it was the left leg that was treated with both calcipotriol and the isopropyl myristate product.

EXAMPLE 2

A 36 year old woman had a chronic problem with red, thick, scaling psoriasis of the palms. She was given a prescription for Dovonex brand of 0.005% calcipotriol ointment to be used on both palms. She was also given a sample container of the 40% isopropyl myristate product of Example 1 to be used as a spray and was asked to use that additionally, but on one palm only. When seen again two weeks later, she was found to have improved only on the palm treated with both products. She had brought both the 40% isopropyl myristate product and the prescription tube with her. On inspection, the prescription product turned out not to be Dovonex, but instead was a product called 0.05% DesOwen ointment that had been dispensed in error. DesOwen is a trademark for desonide, a low potency corticosteroid. In this Example, the combination of the known anti-psoriatic agent 0.05% desonide plus the 40% isopropyl myristate was more effective than the 0.05% desonide by itself.

EXAMPLE 3

Some patients had complained of stinging, burning and dryness experienced when they treated their psoriatic patches with a product containing 0.2% zinc pyrithione, 25% isopropyl myristate, sodium lauryl sulfate, ethanol and water ("25% isopropyl myristate product"). Prescriptions were then written to add 0.05% by weight of fluocinolone acetonide (a corticosteroid) powder to the 25% isopropyl myristate product. The added fluocinolone dissolved easily into the 25% isopropyl myristate product.

The new product that contained both 0.05% fluocinolone and 25% isopropyl myristate produced a marked reduction in the amount of irritation evoked by the 25% isopropyl myristate product and made it much more easily tolerated. In these patients, the combination formulation of the 25% isopropyl myristate product with 0.05% fluocinolone acetonide was more effective in treating the psoriasis than the 25% isopropyl myristate product by itself.

More than 50 patients were treated with the combination formulation of 0.05% fluocinolone acetonide and the 25% isopropyl myristate product. Among these patients there has been a high rate, estimated at more than 80%, of positive response to this combination formulation and it has become for the prescribers the preferred prescription for topical treatment of localized plaque psoriasis. Such a high rate is unusual for treatment of psoriasis with a corticosteroid which is not an ultra high potency corticosteroid. An advantage of this combination formulation is that it avoids the side effect concerns associated with the chronic use of ultra high potency corticosteroids. For most of these 50 patients, the combination formulation was more effective in treating the psoriasis than corticosteroids similar or identical to fluocinolone acetonide by itself.

The results of Examples 1–3 were surprising and unexpected.

Although the preferred embodiments have been described, it is understood that various modifications may be resorted to without departing from the scope of the invention as disclosed and claimed herein.

What is claimed is:

1. A pharmaceutical composition for use in the treatment of psoriasis comprising (a) 0.0001 to 30 weight percent of an anti-psoriatic agent selected from the group consisting of corticosteroids, calcipotriol, retinoids, tar, and mixtures thereof and (b) 15 to 97 weight percent isopropyl myristate, said component (a) being present in an effective anti-psoriatic weight percent, said pharmaceutical composition being a liquid and being in a form suitable for topical administration to a human.

2. A composition according to claim 1, said composition being at least 25 weight percent isopropyl myristate.

3. A composition according to claim 2, said composition being at least 40 weight percent isopropyl myristate.

4. A composition according to claim 2, said composition being 38–60 weight percent isopropyl myristate.

5. A composition according to claim 1, said composition being at least 38 weight percent isopropyl myristate, at least 40 weight percent of said composition being formed from water, ethanol, isopropyl alcohol, or any combination thereof.

6. A composition according to claim 1, said composition being 38–60 weight percent isopropyl myristate, 1.5–10 weight percent water, and 35–60 weight percent ethanol.

7. A method of treating psoriasis comprising topically administering to a human having psoriasis a pharmaceutical composition comprising (a) 0.0001 to 30 weight percent of an anti-psoriatic agent selected from the group consisting of corticosteroids, calcipotriol, retinoids, tar, and mixtures thereof and (b) 15 to 97 weight percent isopropyl myristate, said component (a) being present in an effective anti-psoriatic weight percent, said pharmaceutical composition being a liquid and being in a form suitable for topical administration to a human.

8. A composition according to claim 1, said composition comprising 0.001–5 weight percent corticosteroid.

9. A composition according to claim 8, wherein said composition is at least 25 weight percent isopropyl myristate.

10. A composition according to claim 9, wherein said composition is at least 35 weight percent isopropyl myristate and wherein at least 40 weight percent of said composition is formed from water, alcohol, or any combination thereof.

11. A composition according to claim 10, wherein said alcohol is ethanol, isopropyl alcohol, or a mixture thereof.

12. A composition according to claim 11, said composition being 38–60 weight percent isopropyl myristate, 1.5–10 weight percent water, and 35–60 weight percent ethanol.

13. A composition according to claim 1, wherein said component (a) anti-psoriatic agent is present at 0.005 to 10 weight percent.

14. A composition according to claim 1, wherein at least 40 weight percent of said composition is formed from water, alcohol, or any combination thereof.

15. A composition according to claim 1, said composition comprising 0.0001–0.1 weight percent calcipotriol.

16. A composition according to claim 15, wherein said composition is at least 25 weight percent isopropyl myristate and wherein at least 40 weight percent of said composition is formed from water, alcohol, or any combination thereof.

17. A composition according to claim 1, said composition comprising 0.001–5 weight percent of a corticosteroid other than hydrocortisone.

18. A composition according to claim 17, wherein said composition is at least 25 weight percent isopropyl myristate and wherein at least 40 weight percent of said composition is formed from water, alcohol, or any combination thereof.

19. A composition according to claim 1, wherein at least 40 weight percent of said composition is formed from water, ethanol, isopropyl alcohol, or any combination thereof.

20. A composition according to claim 1, said composition being 30–55 weight percent isopropyl myristate.

21. A composition according to claim 1, said composition consisting essentially of said anti-psoriatic agent, said isopropyl myristate, and at least 40 weight percent water, alcohol or a mixture of water and alcohol.

22. A composition according to claim 21, wherein said anti-psoriatic agent is a corticosteroid other than hydrocortisone.

23. A composition according to claim 21, wherein said anti-psoriatic agent is calcipotriol.

24. A composition according to claim 1, said composition consisting of said anti-psoriatic agent, said isopropyl myristate, surfactant, and at least 40 weight percent of a mixture of water and alcohol.

25. A composition according to claim 24, wherein said anti-psoriatic agent is a corticosteroid other than hydrocortisone.

26. A method according to claim 7, wherein said composition is at least 25 weight percent isopropyl myristate.

27. A method according to claim 7, wherein said composition is at least 40 weight percent isopropyl myristate.

28. A method according to claim 7, wherein said composition is 30–60 weight percent isopropyl myristate.

29. A method according to claim 7, wherein said composition is at least 38 weight percent isopropyl myristate and wherein at least 40 weight percent of said composition is formed from water, ethanol, isopropyl alcohol, or any combination thereof.

30. A method according to claim 7, wherein said composition comprises 38–60 weight percent isopropyl myristate, 1.5–10 weight percent water, and 35–60 weight percent ethanol.

31. A method according to claim 7, wherein said composition comprises 0.001–5 weight percent corticosteroid and at least 35 weight percent isopropyl myristate and wherein at least 40 weight percent of said composition is formed from water, alcohol, or any combination thereof.

32. A method according to claim 7, wherein said composition comprises 0.0001–0.1 weight percent calcipotriol and at least 25 weight percent isopropyl myristate and wherein at least 40 weight percent of said composition is formed from water, alcohol, or any combination thereof.

33. A method according to claim 7, wherein said composition comprises 0.001–5 weight percent of a corticosteroid other than hydrocortisone, wherein said composition comprises at least 25 weight percent isopropyl myristate and wherein at least 40 weight percent of said composition is formed from water, alcohol, or any combination thereof.

34. A method according to claim 7, wherein at least 40 weight percent of said composition is formed from water, alcohol, or any combination thereof.

35. A method according to claim 7, wherein said composition consists essentially of said anti-psoriatic agent, said isopropyl myristate, and at least 40 percent water, alcohol, or a mixture of water and alcohol.

36. A method according to claim 35, wherein said anti-psoriatic agent is calcipotriol or a corticosteroid other than hydrocortisone.

* * * * *